United States Patent [19]

Mueller et al.

[11] Patent Number: 4,992,083
[45] Date of Patent: Feb. 12, 1991

[54] APPARATUS FOR INTERMEDIATE ENRICHMENT OF TRACE SUBSTANCES FROM A GAS STREAM IN A COLD TRAP, AND CHROMATOGRAPHY ARRANGEMENT PROVIDED THEREWITH

[75] Inventors: Klaus-Peter Mueller, Juelich; Jochen Rudolph, Huertgenwald, both of Fed. Rep. of Germany

[73] Assignee: Kernforschungsanlage Juelich Gesellschaft mit beschraenkter Haftung, Juelich, Fed. Rep. of Germany

[21] Appl. No.: 438,078

[22] Filed: Nov. 20, 1989

[30] Foreign Application Priority Data

Nov. 19, 1988 [DE] Fed. Rep. of Germany ....... 3839116
Nov. 24, 1988 [DE] Fed. Rep. of Germany ... 8814619[U]

[51] Int. Cl.$^5$ ............................................. B01D 15/08
[52] U.S. Cl. ......................................... 55/197; 55/208; 55/267; 55/386
[58] Field of Search .................. 55/67, 197, 208, 267, 55/386, 269

[56] References Cited

U.S. PATENT DOCUMENTS

| | | | |
|---|---|---|---|
| 3,608,276 | 9/1971 | Bloomer | 55/197 X |
| 3,683,589 | 8/1972 | Seitz et al. | 55/208 X |
| 3,769,776 | 11/1973 | Berg | 55/67 |
| 4,123,236 | 10/1978 | Hirschfeld et al. | 55/197 |
| 4,154,583 | 5/1979 | Favre et al. | 55/197 X |
| 4,158,630 | 6/1979 | Stearns | 55/386 X |
| 4,469,496 | 9/1984 | Frischmuth et al. | 55/197 |
| 4,732,581 | 3/1988 | Cheh et al | 55/197 X |
| 4,780,116 | 10/1988 | Cheh et al. | 55/197 X |
| 4,881,958 | 11/1989 | Eckhardt et al. | 55/208 X |
| 4,887,434 | 12/1989 | Pilwat et al. | 55/269 X |

FOREIGN PATENT DOCUMENTS 53-014167  2/1978  Japan ..................... 55/208

Primary Examiner—Robert Spitzer
Attorney, Agent, or Firm—Foley & Lardner, Schwartz, Jeffery, Schwaab, Mack, Blumenthal & Evans

[57] ABSTRACT

For intermediate enrichment of trace substances from a gas stream, a cold trap is used which carries a flow and optionally contains an adsorbent material and which is surrounded by a gas-tight double-walled jacket into which cooling fluid from a surrounding cooling bath can penetrate via an extension tube at the bottom. For desorption, the cooling fluid is expelled from the double-walled jacket via compressed air and a valve control. A pipe loop connected to the double-walled jacket and having a heater winding and circulation pump allows rapid heating of the cold trap. A level control apparatus connected to the compressed-air line allows sensitive level adjustment in the bottom extension tube of the double-walled jacket during the desorption phase. Such a cold trap is advantageous, inter alia, in a chromatography arrangement with a separation column and fractionating column of high resolution and sensitivity.

11 Claims, 3 Drawing Sheets

4,992,083

APPARATUS FOR INTERMEDIATE ENRICHMENT OF TRACE SUBSTANCES FROM A GAS STREAM IN A COLD TRAP, AND CHROMATOGRAPHY ARRANGEMENT PROVIDED THEREWITH

BACKGROUND OF THE INVENTION

The invention relates to an apparatus for intermediate enrichment of trace substances from a gas stream in a cold trap which carries a flow and optionally contains an adsorbent material and which, during the enrichment phase, is immersed into cooling fluid in a cooling bath and, for desorption, is subjected to (optionally heated) air or gas, and to a chromatography arrangement provided therewith.

The detection of trace substances in gases, in particular in air, is gaining in importance in view of the increasing pollution of the environment with the most diverse trace substances, some of which are highly toxic or highly harmful to ecology and climatology. The sensitivity of the measuring instruments for the direct detection is here frequently inadequate, so that an intermediate enrichment of the trace substances in a cold trap becomes necessary, which cold trap is immersed into a cooling fluid, from which the cold trap is taken for the actual detection (usually by chromatographic means) with heating.

The applicant has also already provided an apparatus (German Patent No. 3,729,374), in which a U-shaped cold trap surrounded by a heat-insulated container, which is open at the bottom, is immersed into liquified gas as the coolant, which is introduced into the container during the cooling phase, whereas the cold trap is heated up for desorption, coolant being displaced from the container at the same time.

Usually, the coolant used here is liquified nitrogen or liquified air, and the heating-up of the cold trap is carried out especially by electric heating of the cold trap wall consisting of a conductive material.

The detection of particularly small trace substance contents of relatively unstable compounds such as, for example, peroxyacetyl nitrate (PAN), with the aid of such intermediate enrichment has the disadvantages that, at the relatively low temperatures of the liquified gases, considerable quantities of concomitant substances, which can complicate the detection of trace substances, are collected in the cold trap and, that there is a risk of sensitive substances being decomposed by the direct heating of the cold trap.

SUMMARY OF THE INVENTION

It is therefore an object of the present invention to provide an apparatus for intermediate enrichment of trace substances from a gas stream in a cold trap.

A further object is to provide an apparatus in which the enrichment of trace substances is not encumbered by additional accumulation of considerable quantities of concomitant substances and the heating-up for desorption can be achieved under mild conditions and preferably rapidly.

It is also a further object of the present invention to provide an apparatus in which the cold trap does not have to be removed from the cooling fluid for actual detection.

In accomplishing the foregoing objects, there has been provided in accordance with one aspect of the present invention an apparatus according to the present invention is provided, comprising, a gas-tight jacket surrounding a cold trap within a cooling bath, an opening on the lower end of the jacket and means for connecting the interior of the jacket via at least one valve to the atmosphere above the cooling fluid in the cooling bath or to compressed air or gas.

Also, there has been provided in accordance with a second aspect of the present invention, a chromatography arrangement for use in conjunction with the present cold trap apparatus, comprising, a separation column, a fractionating column, feed lines for two carrier gases and means for alternating the operation of the arrangement between variously connected components of the arrangement.

Further objects, features and advantages of the present invention will become apparent from the detailed description of preferred embodiments that follows.

BRIEF DESCRIPTION OF THE DRAWINGS

Types of embodiments of the invention are described below by reference to the attached drawings.

DETAILED DESCRIPTION OF THE PREFERRED EMBODIMENTS

In the apparatus according to the invention, developed for this purpose, the cold trap is surrounded within the cooling bath by a gas-tight jacket, the lower end of which has an opening, in particular an opening extended in the form of a tube, and which is to be connected via at least one valve to the atmosphere above the cooling fluid in the cooling bath or to compressed air or gas.

The enrichment apparatus is particularly appropriate for a chromatography arrangement with a separation column and an upstream fractionating column, as described below and having connecting and changing-over means for an operating mode in which both, in particular, highly volatile gas fractions and components of low volatility are separated off.

Figure 1:
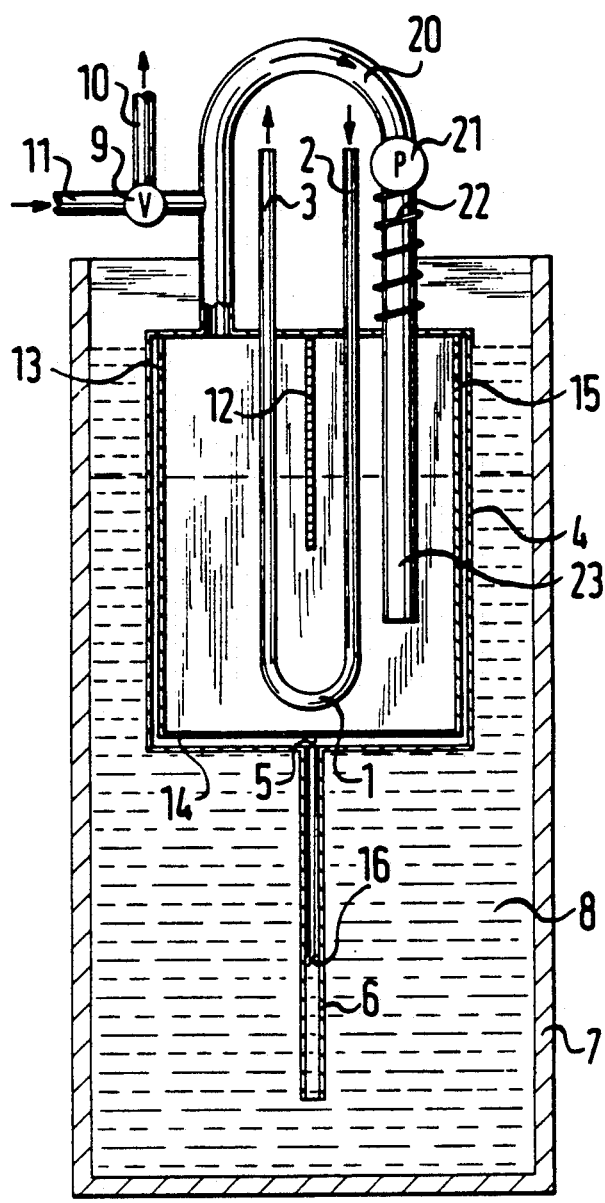
FIG. 1 shows a preferred type of embodiment of the apparatus according to the present invention.

According to FIG. 1, a cold trap 1, which is formed as a U-shaped tube and which carries a flow of the gas to be investigated which enters at 2 and leaves the cold trap again at 3, is surrounded by a gas-tight jacket 4, the lower end of which has an opening 5 which, in particular, is extended as shown by a tube 6 which is open at the bottom.

This arrangement is immersed into a cooling fluid 8 (for example isopropanol having a melting point of 183 K) present in a cooling bath (Dewar vessel) 7. The cooling fluid 8 can be thermostatically controlled in the region of about 200 K. The interior of the gas-tight jacket 4 communicates via at least one valve 9 either with the atmosphere present above the cooling fluid 8, (usually ambient air) (via 10) or with a source of compressed gas, in particular compressed air, by the branch 11.

For the cooling or enrichment phase, the connection of the interior of the jacket to the connection 10 (usually ambient air) via the valve 9 ensures that coolant 8 penetrates from the cooling bath 7 via the tube 6 into the jacket 4 and the cold trap 1 is cooled. A temperature sensor 12 serves for temperature monitoring.

The jacket 4 is provided, preferably in the manner shown as a double-walled jacket, with an inner wall 15 which is perforated at the top and bottom (13,14) and which, during the cooling phase, is filled to the same level with cooling fluid which ensures good heat exchange with the surroundings.

For desorption, the interior of the jacket 4 is connected via the valve 9 to compressed air (branch 11), by means of which the coolant is expelled downwardly from the jacket, so that heating of the cold trap can then take place. The likewise emptied double-walled jacket then ensures heat insulation of the interior of the jacket from the surrounding cooling fluid.

Figure 2:
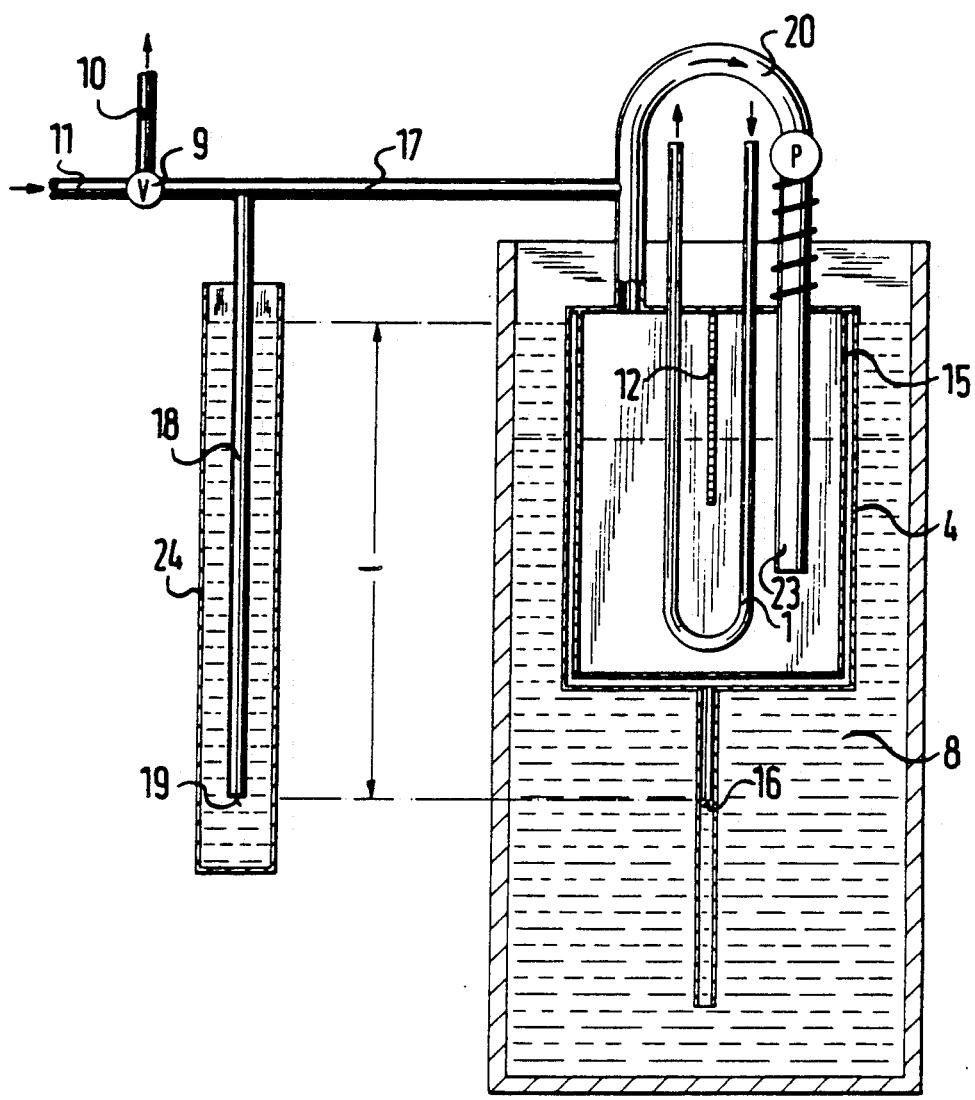
FIG. 2 shows a preferred arrangement for level control of the cooling fluid displaced from the surroundings of the cold trap.

Setting of the fluid level 16 within the extension tube 6 (of, for example, 20 cm length) during the desorption phase can in principle be effected by appropriate pressure control upstream of the valve 9, but with particular advantage an arrangement for setting the fluid level 16 with simultaneous flow through the jacket 4 is provided, as indicated in FIG. 2. Accordingly, the jacket 4 subjected to compressed air communicates with an outward-leading pipe 17, the downward-leading leg 18 of which dips into the fluid to such a depth that the fluid column present above the lower opening 19 balances the height of cooling fluid 1 above the fluid level 16 in the tube 6.

In order to effect rapid heating of the interior of the jacket 4 and hence of the cold trap 1, in particular a pipe loop 20 is provided which comprises an air circulation pump 21 and a heater winding 22.

With particular advantage, the leg 23 located downstream of the pump in the direction of delivery is extended up to the vicinity of the bottom of the jacket, whereby rapid comprehensive heating of the cold trap 1 is achieved. The double-walled jacket (4 with 15) filled with gas during the desorption phase ensures heat insulation between the jacket interior and the cooling fluid 8.

During the desorption phase, heated gas bubbles through the fluid in the level vessel 24 which can be filled with an appropriate fluid of low vapor pressure.

Figure 3:
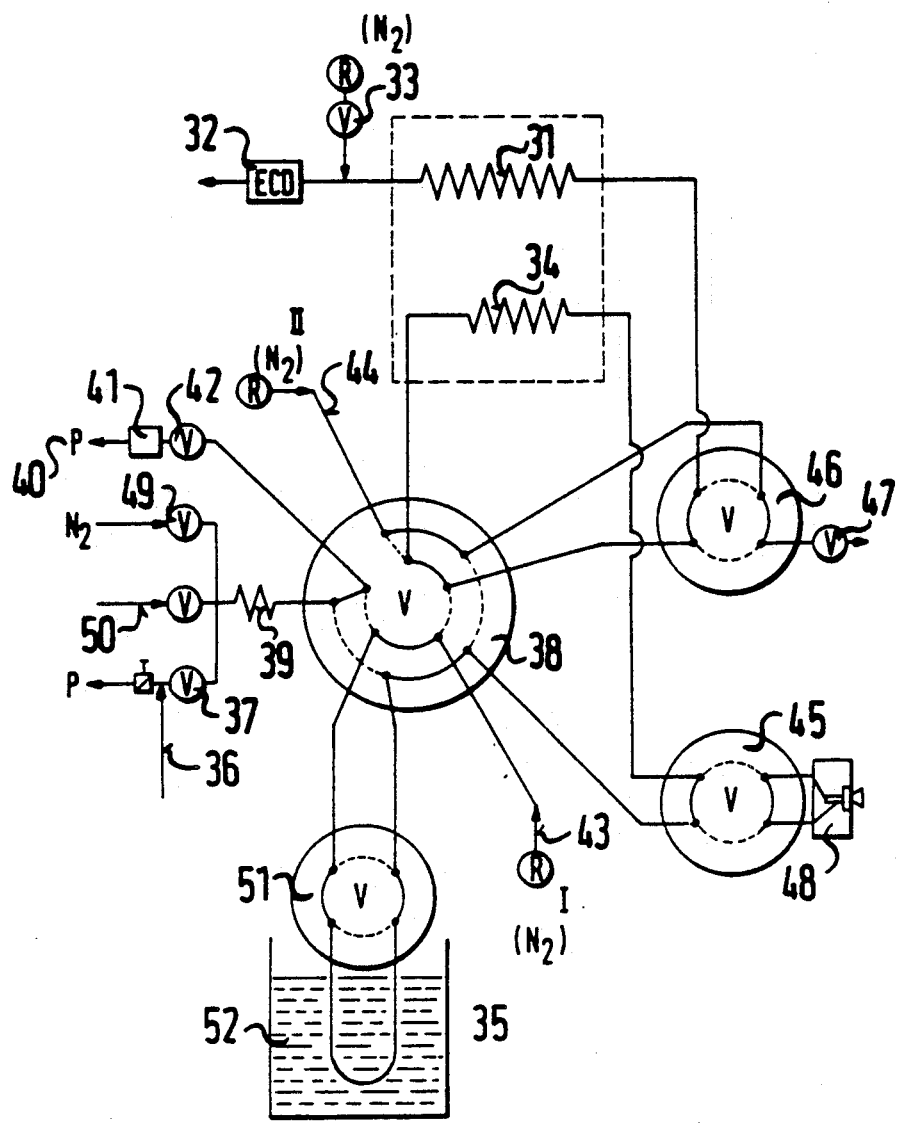
FIG. 3 shows a chromatography arrangement provided with a cold trap.

Advantageously, the apparatus described above for the intermediate enrichment of trace substances can be used in conjunction with a chromatography arrangement such as is illustrated diagrammatically in FIG. 3.

The arrangement shown comprises a separation column 31 with a detector 32 and an inlet 33 for flushing gas as well as a fractionating column 34, an intermediate enrichment cold trap 35, a sample or air inlet 36 with a valve 37, a 10-way valve 38, a compression pipe 39 upstream of the cold trap as well as a pump 40 and a flow controller 41 with an isolation valve 42. The arrangement also includes carrier gas inlets 43 and 44 for carrier gases I and II, as well as the change-over valves 45 and 46, a needle valve 47, if appropriate a liquid injector 48, a valve 49 for compressed-gas feed and, if appropriate, an inlet 50 for calibrating gas. The valve 45 is not always necessary and is provided only for possible liquid injection via 48.

The sample is introduced at 36 via the valve 37 into the compression pipe 39 which, in the position of the 10-way valve 38 shown by dotted lines, communicates with the cold trap 35 with the valve 51 open. This cold trap then also communicates via the valve 42 and the flow controller 41 with the aspiration pump 40 which aspirates the gas, in particular air, into the system.

At the same time, in the position of the 10-way valve shown, carrier gas I is passed via the valve 46 through the separation column 31, and carrier gas II passes via the inlet 44 through the fractionating column 34 and to the outside via 45, 46 and the needle valve 47. The flow parameters of the carrier gases I and II are kept identical so that no pressure surge is caused when the valve 38 is changed over, through which carrier gas I or carrier gas II selectively passes into the separation column.

In this phase, the carrier gas flows through the fractionating column 34 in the direction opposite to that of flow during the analysis phase and carries along the less volatile fractions from the preceding analysis sample.

Appropriately, the fractionating column contains the same adsorbent material as the separation column (for example about 5% of PEG 400 on 80/100 mesh Chromosorb WHP) and its length can amount to, in particular, about 10 to 60% of the length of the separation column.

For the analysis phase, the valves 37 and 42 are closed and the valve 49 is opened for admitting compressed gas ($N_2$ of, for example, about 2.5 bar), by means of which the analysis gas in the cold trap (warmed-up in advance) is compressed, with the aid of the compression pipe 39 (for example of Teflon) having an internal diameter which can approximately correspond to that of the cold trap, the length of the compression pipe matching the decrease in volume from ambient pressure to the increase in pressure. The compressed gas flowing in pushes the analysis sample together in the manner of a piston, so that a sample under system pressure results in the cold trap. After pressure equalization, the valve 49 is closed again. The 10-way valve 38 is then changed over into the position shown in solid lines: carrier gas I then passes into the cold trap and pushes the sample contained therein via the valve 45 into the fractionating column 34, the output from which is initially discharged to the outside via the valve 46 and needle valve 47 (to maintain the system pressure), as long as highly volatile constituents including oxygen are discharged by the column. At the same time, carrier gas II flows via the valve 46 into the separation column 31 maintaining the carrier gas supply thereto.

After a time determined empirically, the valve 46 is changed over and the output of the fractionating column 34 passes into the actual separation column 31 and is subjected therein to the chromatographic analysis.

At this stage, less volatile fractions and, in particular, water are retained in the fractionating column and are expelled in the opposite direction during the subsequent sampling phase. Finally, the cooling bath which is required for the cold trap 34 and by means of which pollutants of low boiling points are accumulated, is indicated by 52.

What is claimed is:

1. An apparatus for intermediate enrichment of trace substances from a gas stream in a cold trap which carries a flow and optionally contains an adsorbent material and which, during the enrichment phase, is immersed into cooling fluid in a cooling bath and, for desorption, is subjected to heated or unheated air or gas, comprising:
    (a) a gas-tight jacket surrounding said cold trap ;
    (b) an opening on the lower end of said jacket; and
    (c) means for connecting the interior of said jacket via at least one valve to the atmosphere above said cooling fluid in said cooling bath or to a compressed gas.

2. The apparatus as recited in claim 1, wherein said opening extends in the form of a tube.

3. The apparatus as recited in claim 1, further comprising means for circulating heated air within said jacket.

4. The apparatus as recited in claim 3, wherein said circulating means comprises a pipe loop with a heater winding and a circulation pump connected to a compressed-air inlet and said jacket.

5. The apparatus as recited in claim 4, further comprising an extension of the leg of said pipe loop, extending down into the bottom region of said jacket, said pump delivering in the direction of said extension.

6. The apparatus as recited in claim 1, further comprising a level control in said jacket, wherein said level control comprises a pipe communicating with the interior of said jacket leading to the outside of said jacket and having a downward-leading leg which is open at the bottom and dips into the fluid to such a depth that the supernatant column of fluid in said downward-leading leg is in equilibrium with the height of the fluid above the fluid level in said extension tube of said jacket.

7. The apparatus as recited in claim 1, wherein said cold trap is a U-tube which comprises a helical winding.

8. The apparatus as recited in claim 1, wherein the side wall and the bottom of said jacket are a double-walled jacket having openings in the inner wall at the upper and lower ends of said jacket.

9. The apparatus as recited in claim 1, further comprising means for thermostatically controlling the cooling fluid.

10. A chromatography arrangement for use in conjunction with the apparatus recited in claim 1, comprising:

(a) a separation column with a detector and an upstream fractionating column;
(b) at least one valve-controlled outlet upstream of said separation column and upstream and downstream of said fractionating column;
(c) feed lines for two carrier gas streams I and II;
(d) means for alternating operation of said arrangement between the independent steps of,
  (i) simultaneously introducing a sample to said cold trap, passing said carrier gas I through said separation column and passing said carrier gas II through said fractionating column,
  (ii) compressing said sample collected in said cold trap and then passing said carrier gas I through said cold trap so that said compressed sample enters said fractionating column, and
  (iii) passing said sample through said fractionating column and then through said separation column, and;
(e) means for temporarily connecting said fractionating column to said valve-controlled outlet for the removal of the most volatile gas fractions from said arrangement.

11. The arrangement as recited in claim 10, wherein said alternating means comprises a 10-way valve operatively connected to an aspiration section, a sample inlet, the inlet and outlet of said enrichment cold trap, said carrier gas feed I, said fractionating column inlet, said valve-controlled outlet valve and said separation column inlet with a change-over valve, said fractionating column outlet and said carrier gas feed II, said 10-way valve providing mean for alternating between the following connections: (A) sample inlet—cold trap —aspiration section; carrier gas feed I—separation column; carrier gas feed II—fractionating column outlet valve and (B) sample inlet —aspiration section; carrier gas feed I—cold trap —fractionating column—separation column or outlet valve; carrier gas feed II—outlet valve.

* * * * *